United States Patent [19]

Williams

[11] Patent Number: Plant 6,198

[45] Date of Patent: Jun. 14, 1988

[54] ROSE PLANT NAMED MINXCO

[76] Inventor: Ernest D. Williams, 1510 Lebanon Ave., Dallas, Tex. 75208

[21] Appl. No.: 857,479

[22] Filed: Apr. 30, 1986

[51] Int. Cl.[4] ..... A01H 5/00

[52] U.S. Cl. ..... Plt./7

[58] Field of Search ..... Plt. 7

*Primary Examiner*—Robert E. Bagwill

[57] ABSTRACT

This invention relates to a new and distinct variety of miniature rose plant primarily identified by the unusual lavender/tan color of the petals, being a blending of mauve and yellow.

1 Drawing Sheet

1

The present invention relates to a new and distinct variety of hardy, dwarf, bush type rose plant of the miniature class; the variety being primarily characterized—as to novelty—by the unusual coloring of the petals, being a blending of mauve and yellow giving a coloring in the lavender/tan range.

The variety is further characterized by:

An abundance of bloom, with flowers usually borne singly, but also several to the stem in loose clusters.

Very fragrant.

A plant which is vigorous, of rounded, upright shape with small semi-glossy to matt foliage with pointed leaflets; the buds and flowers being similar in form and size to Anita Charles (miniature—U.S. Plant Pat. No. 5,110).

The plant, which has a normal height of 10–12 inches or more, can easily be maintained at lesser height by occasional trimming.

A plant which grows and blooms satisfactorily both in greenhouse and outdoors; is good for growing in pots; and provides excellent garden decoration as well as cut flowers.

The present variety of miniature rose was originated by me at my nursery located at Dallas, Tex., under conditions of careful control and observation, as a cross between Angel Face (U.S. Plant Pat. No. 2,792, expired—Floribunda) as the seed parent and Anita Charles (miniature—U.S. Plant Pat. No. 5,110) as the pollen parent.

Subsequent to origination of the vareity I successfully asexually reproduced it at my nursery, located as aforesaid, by cuttings, the reproductions having run true in all respects.

The color photograph illustrates the variety, including the foliage, buds and flowers.

Referring now specifically to the new and distinct variety of miniature rose plant, the following is a detailed description thereof in outline.

Type: Hardy; dwarf; bushy; upright; seedling; greenhouse; outdoors; cut flowers; garden decoration; potted plant.

Class: Miniature.

Variety identification: Minxco (Commercial synonym: Twilight Trail).

Flowers borne: Singly and several together (3 to 5) on slender wirey stems.

Quantity of bloom: Abundant both outside and in greenhouse.

Bud:

2

*Peduncle.*—Medium to long; slender but sturdy; erect; medium green, sometimes tinted bronze (outdoors); with no prickles and few or no short hairs.

*Before calyx breaks.*—Size — small.

*Form.*—Long; pointed; with several foliaceous apendages on surface of bud; with foliaceous parts extending beyond the tip of the bud equal to one-half or less of its length.

*Color.*—Medium to dark green, occasionally tinted with bronze (outdoors).

*As calyx breaks.*—Color — tanish. Opening — opens well in all weather.

Bloom:

*Size when fully open.*—Small, averaging about 30 mm (1¼").

*Petalage.*—Double — averaging about 30–35 petals arranged regularly, plus sometimes several small petaloids.

*Form.*—High centered with petals rolled loosely outward and downward. Open flowers usually show stamens.

Petals: Fairly thick; satiny on inside and on outside surfaces.

*Shape.*—Outside petals, broad lanceolate (nearly round), without acute tip; intermediate — broad lanceolate, sometimes with acute tip; inside — lanceolate.

Color: Newly opened flower from plant grown at Dallas, Tex.

*Outside petal.*—Outside surface — pinkish mauve with yellow, becoming brownish yellow near base. Inside surface — pinkish mauve underlaid with yellow, with darker veining, and becoming more yellow near base.

Overall aspect (effect) being a lavender/tan blend. (Note: The Color Chart has no similar color!).

*Intermediate petal.*—Outside surface similar to outside petal. Inside surface similar to outside petal.

*Inner petal.*—Outside surface — same as intermediate petal; inside surface — same as intermediate petal.

*General color effect.*—Buds and newly opened flowers — unique lavender/tan (mauve blend). Three days open — color similar but less intense.

*Behavior.*—Opens well in all weather. Spent petals drop off.

*Flower longevity* (September 1985).—Plant in pot 4–6 days or longer. Cut flowers at living room temperature 4–5 days or longer.

Reproductive organs:

*Stamens.*—Fair amount.

*Filaments.*—Varying length, medium long.

*Anthers.*—Yellow.

*Pollen.*—Some.

*Pistils.*—Average number.

*Styles.*—Varying length; bunched.

*Ovaries.*—All enclosed in calyx.

*Hips.*—Some.

*Sepals.*—Permanent; spear shaped; recurved.

*Seed.*—Several.

Foliage:

*Leaves.*—Compound of five (sometimes three or seven) leaflets; medium small; leathery; semi-glossy to matt.

*Leaflets.*—Shape: broad, nearly oval; apex acute; base rounded — sometimes acute.

*Color.*—Dark green; new growth — normal (medium) green, sometimes tinted reddish.

*Rachis.*—Medium strength; upper side may have several tiny short hairs; grooved; underside may have several thorns (1–3).

*Stipules.*—Medium to short length; medium width; medium length narrow points which turn out usually at about 45 degrees.

Growth:

*Habit.*—Dwarf; bushy; upright; much branched.

*Growth.*—Free; vigorous; internodes short.

*Canes.*—Medium; slender; sturdy.

*Main stems.*—Color; medium green. Thorns: average. Prickles — none. Hairs — none.

*Branches.*—Color: medium green. Thorns: average; slender; prickles: none. Hairs — none.

The miniature rose plant and its flowers as herein described may vary in slight detail due to climatic, soil and cultural conditions under which the variety may be grown; the present description being of the variety as grown at Dallas, Tex.

The following is claimed:

1. A new and distinct variety of miniature rose plant of hardy, dwarf, bushy, upright, much branched habit, substantially as illustrated and described, characterized by buds and flowers of exhibition form, the color being a blending of yellow and lavender, essentially a mauve/tan color, the petals being lighter color (more gold) on the outside surface, and further characterized by a plant of compact well rounded shape; vigorous, with the main stems and shoots being of average thorniness, the said plant being easy to propagate from cuttings, with an abundance of small semi-glossy to matt foliage and an abundance of flowers borne singly or several to the stem in loose clusters.

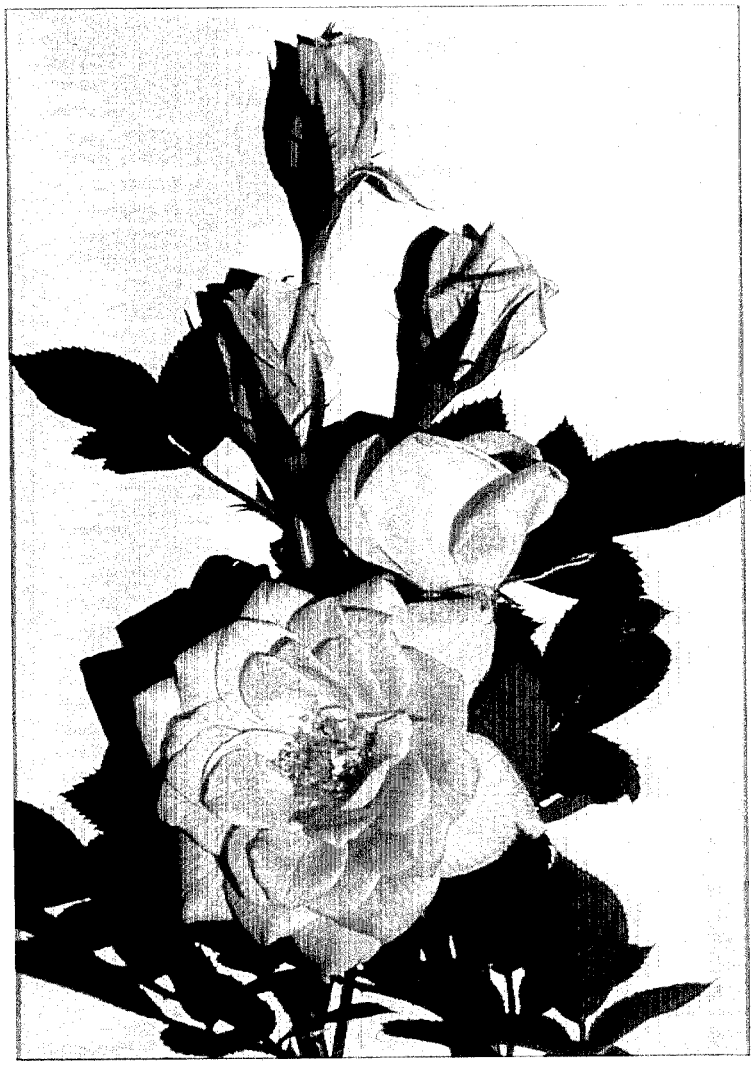

* * * * *